United States Patent
Fralick et al.

(10) Patent No.: US 8,116,842 B2
(45) Date of Patent: Feb. 14, 2012

(54) BIO-PHOTONIC FEEDBACK CONTROL SOFTWARE AND DATABASE

(75) Inventors: John Fralick, Salt Lake City, UT (US); Kathy L. Chapman, legal representative, Salt Lake City, UT (US); David L. Breiter, Orem, UT (US); Jack Peterson, Elk Ridge, UT (US); Mindy Gilbert, Cedar Hills, UT (US); Marvin Distel, Albuquerque, NM (US); Ryan Newman, Elk Ridge, UT (US); Joel Erickson, Spanish Fork, UT (US)

(73) Assignee: NSE Products, Inc., Provo, UT (US)

( * ) Notice: Subject to any disclaimer, the term of this patent is extended or adjusted under 35 U.S.C. 154(b) by 0 days.

(21) Appl. No.: 12/958,528

(22) Filed: Dec. 2, 2010
(Under 37 CFR 1.47)

(65) Prior Publication Data
US 2011/0319730 A1  Dec. 29, 2011

Related U.S. Application Data

(63) Continuation of application No. 10/865,740, filed on Jun. 10, 2004, now abandoned.

(51) Int. Cl.
*A61B 5/00* (2006.01)

(52) U.S. Cl. ........ 600/407; 600/410; 600/476; 600/477; 424/439; 356/301; 356/302; 709/202; 709/203

(58) Field of Classification Search .......... 600/407, 600/410, 476, 477; 705/14, 26, 77, 2; 702/27
See application file for complete search history.

(56) References Cited

U.S. PATENT DOCUMENTS

| | | | |
|---|---|---|---|
| 3,272,766 | A | 9/1966 | Gowman |
| 4,252,709 | A | 2/1981 | Skostins |
| 4,318,057 | A | 3/1982 | Buchwald et al. |
| 4,500,995 | A | 2/1985 | White |
| 4,758,081 | A | 7/1988 | Barnes |
| 4,807,240 | A | 2/1989 | Goldstone |

(Continued)

FOREIGN PATENT DOCUMENTS

EP  0 368 436  5/1990

(Continued)

OTHER PUBLICATIONS

Zhang, Qingguo et al. "Turbidity-free fluorescence spectroscopy of biological tissue," Optics Letters, vol. 25, No. 19, pp. 1451-1453 (Oct. 1, 2000).

(Continued)

*Primary Examiner* — Brian Casler
*Assistant Examiner* — Joel Lamprecht
(74) *Attorney, Agent, or Firm* — Dorsey & Whitney LLP (57) ABSTRACT

A process, apparatus, and method for online control and database collection and management of a computerized detection, tracking, and feedback control system. The system tests for nutrients by Raman scattering effects on skin or other tissues to determine the content of carotenoids or other nutrients as evidenced in that skin. Serum levels of nutrients may vary dramatically with time, but skin tissues may average such nutrition over time. Skin and other tissues may be scanned with light to produce accurate measurements of carotenoids or other nutrients accumulated in the skin based on the Raman scattering affect of those nutrients in the skin. A score can be derived from a properly calibrated bio-photonic scanner to reflect an averaged effective uptake of the detected nutrient (e.g. such as the carotenoid example).

10 Claims, 9 Drawing Sheets

U.S. PATENT DOCUMENTS

| | | | |
|---|---|---|---|
| 4,832,483 | A | 5/1989 | Verma |
| 4,852,579 | A | 8/1989 | Gilstad et al. |
| 4,858,238 | A | 8/1989 | Cardimona |
| 4,975,581 | A | 12/1990 | Robinson et al. |
| 5,034,228 | A | 7/1991 | Meybeck et al. |
| 5,124,313 | A | 6/1992 | Schaeffer et al. |
| 5,202,826 | A | 4/1993 | McCarthy |
| 5,243,983 | A | 9/1993 | Tarr et al. |
| 5,275,168 | A | 1/1994 | Reintjes et al. |
| 5,290,605 | A | 3/1994 | Shapira |
| 5,303,026 | A | 4/1994 | Strobl et al. |
| 5,304,170 | A | 4/1994 | Green |
| 5,310,563 | A | 5/1994 | Curtis et al. |
| 5,346,488 | A | 9/1994 | Prince et al. |
| 5,348,018 | A | 9/1994 | Alfano et al. |
| 5,418,797 | A | 5/1995 | Bashkansky et al. |
| 5,421,337 | A | 6/1995 | Richards-Kortum et al. |
| 5,432,610 | A | 7/1995 | King et al. |
| 5,449,376 | A | 9/1995 | Callahan |
| 5,451,785 | A | 9/1995 | Faris |
| 5,452,723 | A | 9/1995 | Wu et al. |
| 5,537,314 | A | 7/1996 | Kanter |
| 5,552,997 | A | 9/1996 | Massart |
| 5,553,616 | A | 9/1996 | Ham et al. |
| 5,556,612 | A | 9/1996 | Anderson et al. |
| 5,567,628 | A | 10/1996 | Tarcha et al. |
| 5,579,773 | A | 12/1996 | Vo-Dinh et al. |
| 5,590,660 | A | 1/1997 | MacAulay et al. |
| 5,643,623 | A | 7/1997 | Schmitz et al. |
| 5,657,754 | A | 8/1997 | Rosencwaig |
| 5,666,223 | A | 9/1997 | Bennett et al. |
| 5,697,373 | A | 12/1997 | Richards-Kortum et al. |
| 5,730,714 | A | 3/1998 | Guy et al. |
| 5,733,507 | A | 3/1998 | Zakim |
| 5,734,838 | A | 3/1998 | Robinson et al. |
| 5,811,804 | A | 9/1998 | Van Blitterswijk et al. |
| 5,873,831 | A | 2/1999 | Bernstein et al. |
| 6,134,533 | A | 10/2000 | Shell |
| 6,205,354 | B1 | 3/2001 | Gellermann et al. |
| 6,408,281 | B1 | 6/2002 | Shell et al. |
| 6,415,265 | B1 | 7/2002 | Shell et al. |
| 6,421,648 | B1 | 7/2002 | Gagnon et al. |
| 6,595,929 | B2 | 7/2003 | Stivoric et al. |
| 6,621,574 | B1 | 9/2003 | Forney et al. |
| 6,690,966 | B1 | 2/2004 | Rava et al. |
| 7,039,452 | B2 | 5/2006 | McClane et al. |
| 7,088,233 | B2 | 8/2006 | Menard |
| 7,262,842 | B2 | 8/2007 | Ermantraut et al. |
| 7,365,839 | B2 | 4/2008 | Ferguson et al. |
| 2002/0022775 | A1 | 2/2002 | Finkelshteins |
| 2002/0072932 | A1 | 6/2002 | Swamy |
| 2002/0098588 | A1 | 7/2002 | Sammak et al. |
| 2002/0118361 | A1 | 8/2002 | Cadell et al. |
| 2002/0133080 | A1 | 9/2002 | Apruzzese et al. |
| 2003/0030798 | A1 | 2/2003 | Samsoondar et al. |
| 2003/0130579 | A1 | 7/2003 | McClane et al. |
| 2003/0148542 | A1 | 8/2003 | Pawlak et al. |
| 2004/0254479 | A1 | 12/2004 | Fralick et al. |
| 2005/0197580 | A1 | 9/2005 | Ferguson et al. |
| 2005/0197581 | A1 | 9/2005 | Ferguson et al. |
| 2005/0197582 | A1 | 9/2005 | Ferguson et al. |
| 2005/0278184 | A1 | 12/2005 | Fralick et al. |
| 2006/0092411 | A1 | 5/2006 | Ferguson et al. |

FOREIGN PATENT DOCUMENTS

| | | |
|---|---|---|
| EP | 0 607 941 | 7/1994 |
| EP | 0722692 A1 | 7/1996 |
| JP | 03-120445 | 5/1991 |
| JP | 10-153529 | 9/1998 |
| JP | 2002-286628 | 10/2002 |
| JP | 2003-507088 | 2/2003 |
| JP | 2003-108679 | 4/2003 |
| JP | 2003-530184 | 10/2003 |
| TW | 552126 B | 9/2003 |
| TW | 558635 B | 10/2003 |
| WO | 92/10131 | 6/1992 |
| WO | 92/15008 | 9/1992 |
| WO | 00/78217 | 12/2000 |
| WO | 01/78577 | 10/2001 |
| WO | 02/43585 | 6/2002 |
| WO | 02/063269 | 8/2002 |

OTHER PUBLICATIONS

API-American Polarizers, Inc., Linear Polarizers, Near Linear Polarizer-HR, http://www.apioptics.com/linear12.htm., pp. 1-4 (Feb. 3, 2004).

Bays, R. et al. "Three-dimensional optical phantom and its application in photodynamic therapy," Lasers in Surgery and Medicine, Wiley-Liss, New York, US, vol. 21, No. 3, pp. 227-234 (Jan. 1, 1997).

Bell, S.E.J. et al. "Extracting Raman spectra from highly fluorescent samples with 'Scissors' (SSR, Shifted-Subtracted Raman Spectroscopy)," Raman Spectroscopy, Spectroscopy Europe 14/6, pp. 1-4 (2002).

Berendshot, Tos T. J. M., et al., "Influence of Lutein Supplementation on Macular Pigment, Assessed with Two Objective Techniques," IOVS, vol. 41, No. 11, pp. 3322-3326 (Oct. 2000).

Bone, R.A., Landrum, J.T., and Cains, A, "Optical Density Spectra of the Macular Pigment In Vivo and In Vitro," Vision Res., vol. 32, No. 1, pp. 105-110, 1992.

Brenan, C.J.H. et al. "Volumetric Raman microscopy through a turbid medium," Journal of Raman Spectroscopy, vol. 27, pp. 561-571 (1996).

Brody, J.E., "Health Factor in Vegetables Still Elusive," The New York Times, Section C, p. 1, (Feb. 21, 1995).

Cerussi, A.E. et al. "Chromophore detection by fluorescence spectroscopy in tissue-like phantoms," SPIE, 2979, pp. 139-150 (1997).

Dubois, D. et al. "Moldable tissue equivalent bolus for high-energy photon and electron therapy," Medical Physics, vol. 23, No. 9: pp. 1547-1549 (1996).

Elsner, Ann E., et al, "Foveal Cone Photopigment Distribution: Small Alterations Associated with Macular Pigment Distribution," IOVS, vol. 39, No. 12, pp. 2394-2404 (Nov. 1998).

Firbank and D.T. Delpy, M. "A design for a stable and reproducible phantom for use in near infra-red imaging and spectroscopy," Physics in Medicine and Biology, Taylor and Francis Ltd., London, GB, vol. 38, No. 6, pp. 847-853 (Jun. 1, 1993).

Firbank, Michael et al. "An improved design for a stable and reproducible phantom material for use in near-infrared spectroscopy and imaging," Physics in Medicine and Biology, Taylor and Francis Ltd., London, GB, vol. 40, No. 5, pp. 955-961 (Jan. 1, 1995).

Gellermann, W. et al. "Noninvasive laser Raman detection of carotenoid antioxidants in living human skin," SPIE, vol. 4244, pp. 36-44 (2001).

Gill, D. et al. "Resonance Raman Spectra of Conjated Polyvinylenes in Dichroic Polarizing Sheets (Polaroid KN-42)," Chemical Physics Letters, vol. 8, No. 6, pp. 634-636 (Mar. 15, 1971).

Gniadecka, Monika et al. "Distinctive Molecular Abnormalities in Benign and Malignant Skin Lesions: Studies by Raman Spectroscopy," Photochemistry and Photobiology, 66(4): 418-42 (1997).

Hammond, B.R., Fuld, K., and Curran-Celentano, J., "Macular Pigment Density in Monozygotic Twins," Invest. Ophthalmo. Vis. Sci., vol. 36, No. 12, pp. 2531-2541 (Nov. 1995).

Handelman, G.J., Snodderly, D.M., Krinsky, N.L., Russett, M.D., and Adler, A.J., "Bilogical Control of Primate Macular Pigment," Inv. Ophthalmol. Vis. Sci., vol. 32, No. 2, pp. 257-267 (Feb. 1991).

Hata, T. R. et al. "Non-invasive Raman spectroscopic detection fo carotenoids in human skin", Journal of Investigative Dermatology, vol. 115, No. 3, pp. 441-448 (2000).

Hunt, S. et al. "Spectroscopic characterization of low molecular weight fluids from silicone elastomers," Journal of Macromolecular Science, Pure and Applied Chemistry, vol. A39, No. 9, pp. 1007-1024 (2002).

Lambert, J. L. et al. "Measurement of aqueous glucose in a model anterior chamber using Raman spectroscopy", Journal of Raman Spectroscopy, vol. 33, pp. 524-529 (2002).

Land, Edwin H. "Some aspects of the development of sheet polarizers," Journal of the Optical Society of America, vol. 41, No. 12, pp. 957-963 (Dec. 1951).

Linear and Circular Polarizers, Vikniti Display Enhancement, 3M Corporation, pp. 1-8 (2001).

Lualdi, M. et al. "A phantom with tissue-like optical properties in the visible and near infrared for use in photomedicine", Lasers in Surgery and Medicine, vol. 28, pp. 237-243 (2001).

Makropoulou, M.I. et al. "Quantitative estimation of absorbing chromophores in tissue simulators based on laser induced spectroscopy and scattering measurements," SPIE vol. 4162, pp. 76-85 (2000).

Material Safety Data Sheet, Dow Corning® 3179 Dilatant Compound, pp. 1-6 (Jul. 7, 1997).

Pharmanex Biophotonic Scanner Operating manual, pp. 1-38 (Mar. 2003).

Pogue, B. W. et al. "Review of tissue simulating phantoms for optical spectroscopy, imaging, dosimetry," Journal of Biomedical Optics, SPIE, P.O. Box 10, Belingham, WA, 98227-0010, vol. 11, No. 4, pp. 41102 (Jul. 1, 2006).

Polyzois, G.L. et al. "Physical properties of a silicone prosthetic elastomer stored in simulated skin secretions," Journal of Prosthetic Dentistry, vol. 83, No. 5, pp. 572-577 (2000).

Schalch, Wolfgang, "Carotenoids in the Retina—A Review of Their Possible Role in Preventing or Limiting Damage Caused by Light and Oxygen," Free Radicals and Aging, Basel, Switzerland: Birkhauser Verlag, pp. 280-298 (1992).

Schut, Tom C. Bakker et al. "Intracellular Carotenoid Levels Measured by Raman Microspectroscopy: Comparison of Lymphocytes from Lung Cancer Patients and Healthy Individuals," Int. J. Cancer (Pred. Oncol): 74, 20-25 (1997).

Seddon, J.M., Ajani, U.A., Sperduto, R.D., Hiller, R., Blair, N., Burton, T.C., Farber, M.D., Gragoudas, E.S., Haller, Jr., Miller, D.T., Yannuzzi, L.A., and Willet, W., "Dietary Carotenoids, Vitamins A, C and E, and Advanced Age-Related Macular Degeneration," J. Am. Med. Assoc., vol. 272, No. 18, pp. 1413-1420, (Nov. 9, 1994).

Shim, M. G. et al. "Study of Fiber-Optic Probes for in vivo Medical Raman Spectroscopy", Applied Spectroscopy, vol. 53, No. 6, pp. 619-627 (1999).

Wagnieres, G. et al. "An optical phantom with tissue-like properties in the visible for use in PDT and fluorescence spectroscopy," Physics in Medicine and Biology, Taylor and Francis Ltd., London, GB, vol. 42, No. 7, pp. 1415-1426 (Jul. 1, 1997).

Wu, J. et al. "Three-dimensional imaging of objects embedded in turbid media with fluorescence and Raman spectroscopy," Applied Optics, vol. 34, No. 18, pp. 3425-3429 (1995).

BIO-PHOTONIC FEEDBACK CONTROL SOFTWARE AND DATABASE

This application is a continuation of U.S. patent application Ser. No. 10/865,740, filed Jun. 10, 2004, entitled "Bio-Photonic Feedback Control Software and Database," the content of which is hereby incorporated in its entirety by reference.

BACKGROUND

1. The Field of the Invention

This invention relates to digital computers and photonic scanners, and more particularly, to unique apparatus and methods for timely, computerized, detection, tracking, and feedback control of the biological uptake of targeted nutrients.

2. The Background Art

Electronics and optical measurement systems are broad and varied. Systems exist for detection of optics by virtue of radar signatures, infrared signatures, and other spectral signatures in radio frequency ranges.

In the area of optics and detectors, U.S. Pat. No. 6,205,354 B1 issued Mar. 20, 2001 to Gellerman et. al. is directed to a method and apparatus for non-evasive measurement of carotenoids and related chemical substances and biological tissue. This patent is incorporated herein by reference. The method and apparatus of Gellerman et al. provide a non-invasive, rapid, accurate, and safe determination of carotenoid levels, which, in turn, can provide diagnostic information regarding risk of disease or markers for conditions, such as levels of carotenoids or other antioxidant compounds in the body. The method and apparatus Resonance Raman Spectroscopy to measure the levels of carotenoids and similar substances in tissue.

Laser light is directed upon an area of tissue of interest. A small fraction of the scattered light is scattered inelastically, producing the carotenoid Raman signal at a different frequency than the incident laser light. The Raman signal is collected, filtered, and measured. The resulting Raman signal can be analyzed such that the background fluorescent signal is subtracted and the results displayed and compared with known calibration standards.

BRIEF SUMMARY AND OBJECTS OF THE INVENTION

A system and method in accordance with the invention may provide a system for control and communication between various computer systems. The system may include a laser illumination and detection system controller and a computer to process the signals of the detector. The system make take data, remove error, compensate for background noise, fit the data to a curve, report the data, and manage a database of the data.

A computer may be programmed to provide controls for the laser scanner and detection system, along with software to control the prompting and instruction of an operator, thus minimizing the skill level required of an operator. That is, much instrumentation is created strictly for the use of those highly skilled in the science to which it pertains. Moreover, much instrumentation is sufficiently complex, with only rudimentary controls, thus requiring a high level of skill and knowledge of both the science and the hardware in order to conduct operations. In a method and apparatus in accordance with the invention, a user interface programmed into a computer connected to a laser scanner may provide for simplified operation by a non-professional and non-technical operator.

Accordingly, the scanner takes data, provided to the master or host computer, and processes that data to determine the intensity of a Raman-Scattering response of the skin of a subject, as a result of laser illumination in a particular spectral band. The computer thus processes the data and provides a display to a user or operator regarding the content of the skin of a subject. For example, the carotenoid level may be identified directly, or identified in a relative sense as a score that may be compared with previous and subsequent scanning results.

The master computer may log data and upload it to a centrally based computer. For example, over a direct link or a world wide web link, the master computer may upload data regarding one or more scanning sessions to the central computer. Thus, many subjects over long periods of time may be tracked and recorded in a database. The central computer facility may track subjects, operators, sellers of nutritional supplements, organizations, entities, and individuals.

BRIEF DESCRIPTION OF THE DRAWINGS

The drawings depict only typical embodiments in accordance with the invention and are, therefore, not to be considered limiting of its scope.

DETAILED DESCRIPTION OF THE PREFERRED EMBODIMENTS

The following more detailed description of the embodiments of systems and methods in accordance with the present invention, as represented in the Figures, is not intended to limit the scope of the invention, as claimed, but is merely representative of certain examples of presently contemplated embodiments in accordance with the invention. Like parts are designated by like numerals throughout.

Many of the functional units described in this specification have been labeled as modules, executables, systems, servers, and the like in order to more particularly emphasize their implementation independence. For example, modules may be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module. For example, a module of executable code may be a single instruction, or many instructions, and may even be distributed over several different code segments, among different programs, and across several memory devices.

Modules may also be implemented in hardware as electronic circuits comprising custom VLSI circuitry, off-the-shelf semiconductors such as logic chips, transistors, or other discrete components. A module may also be implemented in programmable hardware devices such as field programmable gate arrays, programmable array logic, programmable logic devices or the like.

Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 1:
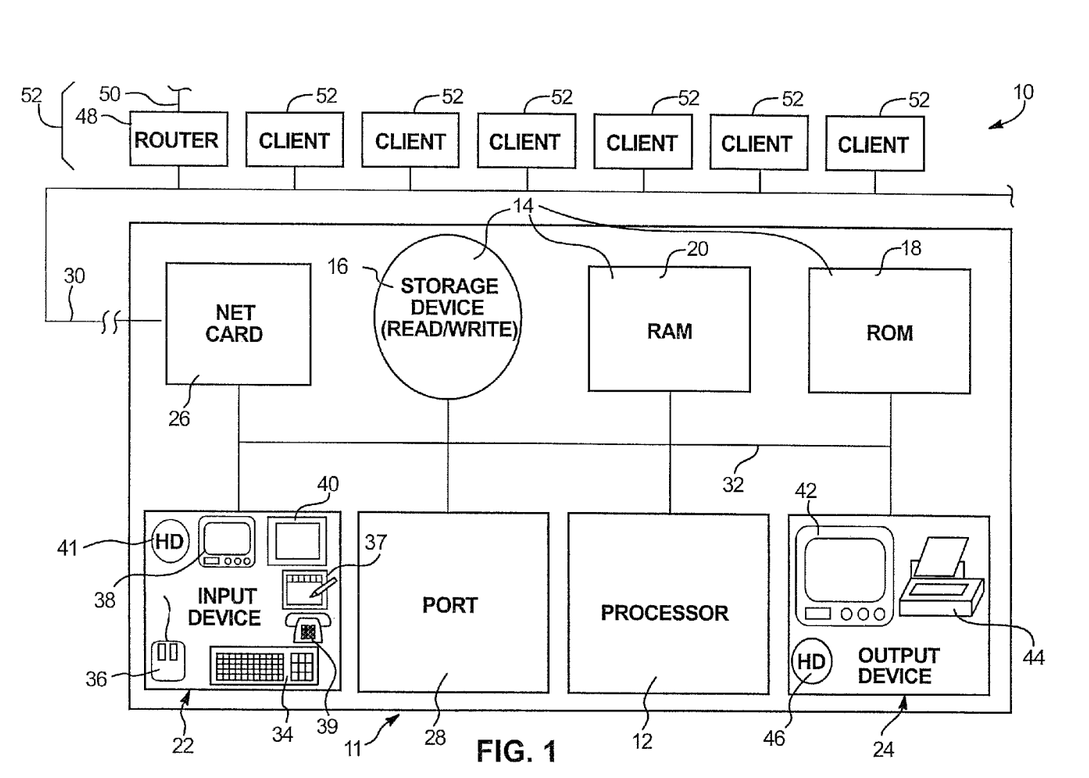
FIG. 1 is a schematic block diagram of a digital computer system such as may be used in various components in an apparatus and method in accordance with the present invention.

Referring to FIG. 1, an apparatus 10 may implement the invention on one or more nodes 11, (client 11, computer 11) containing a processor 12 (CPU 12). All components may exist in a single node 11 or may exist in multiple nodes 11, 52 remote from one another. The CPU 12 may be operably connected to a memory device 14. A memory device 14 may include one or more devices such as a hard drive or other non-volatile storage device 16, a read-only memory 18 (ROM 18) and a random access (and usually volatile) memory 20 (RAM 20 or operational memory 20).

The apparatus 10 may include an input device 22 for receiving inputs from a user or from another device. Similarly, an output device 24 may be provided within the node 11, or accessible within the apparatus 10. A network card 26 (interface card) or port 28 may be provided for connecting to outside devices, such as the network 30.

Internally, a bus 32, or plurality of buses 32, may operably interconnect the processor 12, memory devices 14, input devices 22, output devices 24, network card 26 and port 28. The bus 32 may be thought of as a data carrier. As such, the bus 32 may be embodied in numerous configurations. Wire, fiber optic line, wireless electromagnetic communications by visible light, infrared, and radio frequencies may likewise be implemented as appropriate for the bus 32 and the network 30.

Input devices 22 may include one or more physical embodiments. For example, a keyboard 34 may be used for interaction with the user, as may a mouse 36 or stylus pad 37. A touch screen 38, a telephone 39, or simply a telecommunications line 39, may be used for communication with other devices, with a user, or the like. Similarly, a scanner 40 may be used to receive graphical inputs, which may or may not be translated to other formats. The hard drive 41 or other memory device 41 may be used as an input device whether resident within the node 11 or some other node 52 (e.g. 52, 54, etc.) on the network 30, or from another network 50.

Output devices 24 may likewise include one or more physical hardware units. For example, in general, the port 28 may be used to accept inputs into and send outputs from the node 11. Nevertheless, a monitor 42 may provide outputs to a user for feedback during a process, or for assisting two-way communication between the processor 12 and a user. A printer 44, a hard drive 46, or other device may be used for outputting information as output devices 24.

In general, a network 30 to which a node 11 connects may, in turn, be connected through a router 48 to another network 50. In general, two nodes 11, 52 may be on a network 30, adjoining networks 30, 50, or may be separated by multiple routers 48 and multiple networks 50 as individual nodes 11, 52 on an internetwork. The individual nodes 52 (e.g. 11, 48, 52, 54) may have various communication capabilities.

In certain embodiments, a minimum of logical capability may be available in any node 52. Note that any of the individual nodes 11, 48, 52, 54 may be referred to, as may all together, as a node 11 or a node 52. Each may contain a processor 12 with more or less of the other components 14-46.

A network 30 may include one or more servers 54. Servers may be used to manage, store, communicate, transfer, access, update, and the like, any practical number of files, databases, or the like for other nodes 52 on a network 30. Typically, a server 54 may be accessed by all nodes 11, 52 on a network 30. Nevertheless, other special functions, including communications, applications, directory services, and the like, may be implemented by an individual server 54 or multiple servers 54.

In general, a node 11 may need to communicate over a network 30 with a server 54, a router 48, or nodes 52. Similarly, a node 11 may need to communicate over another network (50) in an internetwork connection with some remote node 52. Likewise, individual components 12-46 may need to communicate data with one another. A communication link may exist, in general, between any pair of devices.

Figure 2:
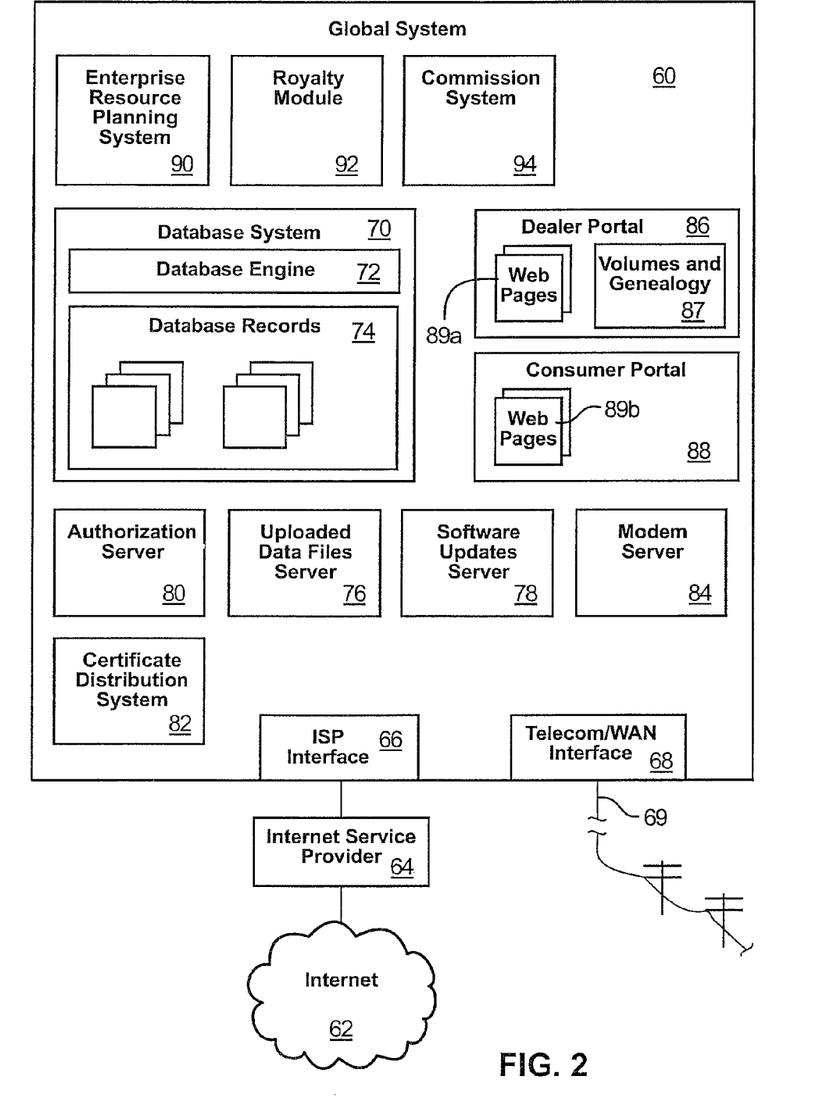
FIG. 2 is a schematic block diagram of a system operable over a system of computers for managing a consumer scanning process.

Referring to FIG. 2, in one embodiment, a system 60 may include various elements of hardware and software in order to implement integration of marketing, tracking of management structures, tracking and execution of compensation, consumer testing and motivation, allocation and tracking of royalty payments, and delivery of nutritional supplements. In one embodiment, a system 60 may include hardware and software suitable to connect to the Internet 62. For example, an Internet service provider 64 may connect through an Internet service provider (ISP) interface 66 to the system 60. Alternatively, or in addition, a telecommunications interface 68 may connect to a conventional telecommunications network 69. In either event or both, the system 60 provides for communication with a network of customers, operators, dealers, managers, suppliers, and so forth.

The database system 70 may be configured to operate in any of a host of modes. For example, object-oriented databases may embed both executables and attributes (operational data) into a single object associated with a particular function, purpose, entity or the like. Similarly, relational databases may operate by virtue of tables populated and managed by independent executables or database engines.

Regardless of whether a database engine 72 is independent from database records 74 or embedded such that the database engine 72 and database records 74 are implemented with individual objects as executables and attributes, respectively, is not determinative. The database system 70 provides the functionality of a database engine 72 capable of moving data in and out of database records 74 and providing for searching, indexing, and so forth of the database records 74.

In certain embodiments, a server 76 may be programmed in software, hardware, or both to handle uploaded data files received from operators operating in accordance with the invention. For example, data files to be received for processing, or for inclusion directly into the database 74 may be uploaded from the Internet 62 or from a telecommunications network 69 from other users (customers, dealers, operators, etc.) into the server 76.

Software updates may be needed for interacting with the system 60 or for software for operating a scanner (see FIGS. 3-5, 7, scanner 102, for example). A server 78 may provide software updates to be downloaded to those in need, such as customers, operators especially, dealers or the like for whom software may be available. Typically, software updates may be provided by the server 78 to operators in order to provide the most recent operating characteristics for the scanner 102.

In certain presently contemplated embodiments, an authorization server 80 may manage and provide authorizations to operators, in order to properly conduct scans using the scanner 102. That is, for example, the intellectual property associated with the scanner is the subject of various patents, licenses, ownership, and the like. Accordingly, several mechanisms may be implemented in order to obtain financial returns on the efficacious use of a scanner 102. For example, if royalties are to be provided on the basis of use of a scanner 102, then the authorization server 80 may allocate, track, and otherwise control use, in order that royalties may be based upon use.

If machines are sold, royalties may be paid based on the sale price of a scanner 102. Thus, an authorization server 80 may be tasked with responsibilities for allocating authorization on an ongoing or on a specific incident basis. Depending on the architecture selected, the servers 76, 78, 80 may all be connected to the database system 70. In an alternative embodiment, the data files server 76 may be connected to the database system 70 and may communicate with the authorization server 80 in order to properly perform the controlling functions thereof. Similarly, the software update server 78 may stand independently, or may be connected to other modules or elements of the system 60 in order to integrate the providing, tracking, and accounting for various services.

The system 82 may actually be another server 81 or a standalone hardware system, or simply be embodied in executables that coordinate with or are incorporated within the authorization server 80.

Similarly, the server 76 may connect to the authorization server 80, with the authorization server 80 providing the gate keeping function, and serving to an operator with the necessary authorization in exchange for the files to be uploaded to the server 76. Thus, a variety of connection and control schemes may be implemented.

In one embodiment, the server 80 may be the web server and forward to the database 70 from the server 76 the files uploaded to the server 76 by the computer 100 and operator. The planning system 90 may incorporate the software, data, or both that allocates, manages, tracks, and accounts for the resources of the enterprise served by the system 60.

The enterprise resource planning system 90 may contain or create the plan, formula, or the control also for the allocation of payments or other resources in a system. The system 90 may provide to the database system 70 periodic updates of the plan.

A royalty module 92 may be an executable, system of objects, a server, or the like that provides for royalty controls and data for licensed technology. For example, patented scanners 102 may pay royalties by a schedule provided by, contained in, stored by, created by, enforced by, or delivered by the royalty module 92.

Similarly, a commission system 94 may contain, create, store, generate, allocate, control, deliver, or enforce a schedule of commissions, bonuses, and other financial payments. The authorization server 80, the certificate distribution system 82, as well as the uploaded data files server 76 and the software updates 78 handle the information data resources flowing into and out of the system 60. The volumes and genealogy module 87 is responsible for publishing the allocations of the volumes of sales, and the information regarding the relationships between networks of dealers, operators, and the like.

The dealer portal 86 may be embodied in a web server as software, hardware, or both within the system 60. The entire system 60 may be hosted on a single computer, wherein each module or element is simply a programmed functionality, such as a software application.

The consumer portal 88 may likewise publish web pages 89 (e.g. 89a, 89b) for consumers. That is, the consumer portal 88 may allow a consumer to track purchases, scanning data from various inventories executed by a scanner 102, product information, dealer contact information, and so forth. A consumer portal 88 may be available to all consumers in general, specific consumers having authorization, or a combination thereof, as allocated by software, security, rights, and so forth.

In certain embodiments, a modem server 84 may provide a bank of modems for access by computers connecting through a telecommunications network 69. Accordingly, a modem server 84 may be operable within the system 60 through the telecommunication or wide area network interface 68.

Figure 3:
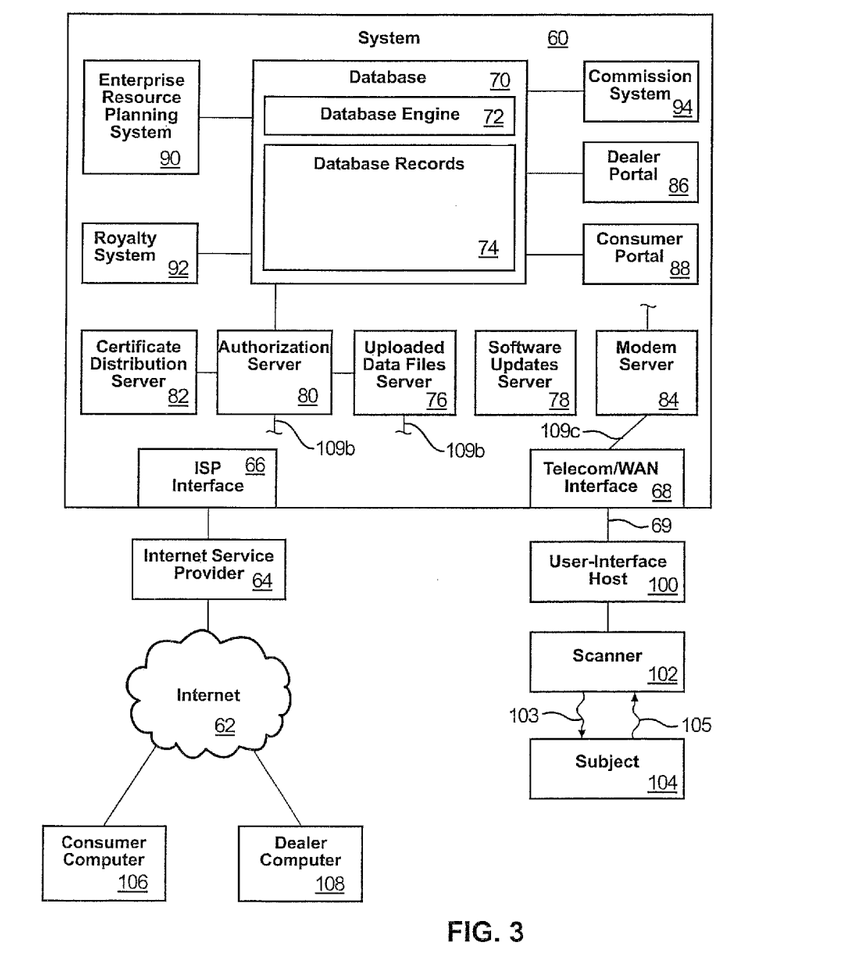
FIG. 3 is a schematic block diagram of an alternative embodiment of a seamless, global, compensation system operating both over the Internet and through direct connection to the system.

Referring to FIG. 3, one embodiment of the system 60 may include a user-interface host 100 connecting over a telecommunications network 69 to a telecommunications interface 68. In some embodiments, the interface 68 may be referred to as a wide area network (WAN) interface 68. Accordingly, the user interface 100 may be a computer, such as a desktop computer, a laptop computer, a personal digital assistant (PDA), or other processor. The user-interface 100 may be a portable, digital computer dedicated to the control and operation of the scanner 102.

The scanner 102 may be configured in accordance with the technology in U.S. Pat. No. 6,205,354 to Gellerman et. al. incorporated herein by reference. The scanner 102 directs a radiation beam 103 in a suitable spectrum onto a subject 104. A subject 104 may be, for example, the skin of a hand or arm. Due to Raman-Scattering, a shifted wavelength of light is returned from the input spectrum 103, as a beam 105. The beam 105 is accordingly detected by the scanner 102 and the data from the detector is processed accordingly, as discussed herein below.

In the illustrated embodiment of FIG. 3, a user-interface host 100 connects by a telecommunication interface 68 directly to the system 60. The information provided by the scanner to the host 100 may be received by the system 60 over a direct line, or over the Internet 62.

Meanwhile, a consumer computer 106 may connect to the Internet 62 in order to access from the system 60 the consumer portal 88. For example, the system 60 may engage through an Internet service provider 64 to publish web pages 89 over a consumer portal 88 on the Internet 62. These web pages 89 may be accessed by a consumer through the consumer's computer 106.

Similarly, a dealer computer 108 in possession of a dealer in nutritional supplements, for example, can connect to the Internet 62 in order to access a dealer portal 86. The dealer portal 86 may provide to the dealer computer 108 the volumes and genealogy programs 87 or data. FIG. 3 shows the database 70 as a "centerpiece" of the system 60, receiving and exchanging information with the enterprise resource planning system 90 and the royalty system 92. Similarly, the database exchanges information with the commission system 94 and the consumer portal 88. Intervening applications or connections may be implemented as appropriate.

In the illustrated embodiment, the dealer portal 86 may have access to the commission system 94 in order to publish to authorized dealers the information for which those dealers are authorized. Some methods of security may be implemented in a typical system 60 in order to provide secure access by only those entitled to receive it.

The authorization server 80 may be connected over a line 109a to the telecommunication interface 68. The uploaded data server 76 may connect over a line 109b to the telecommunication interface 68. A suitable connection scheme and management scheme may be used to optimize the flow of data, the processing thereof, and the serving of appropriate information.

Figure 4:
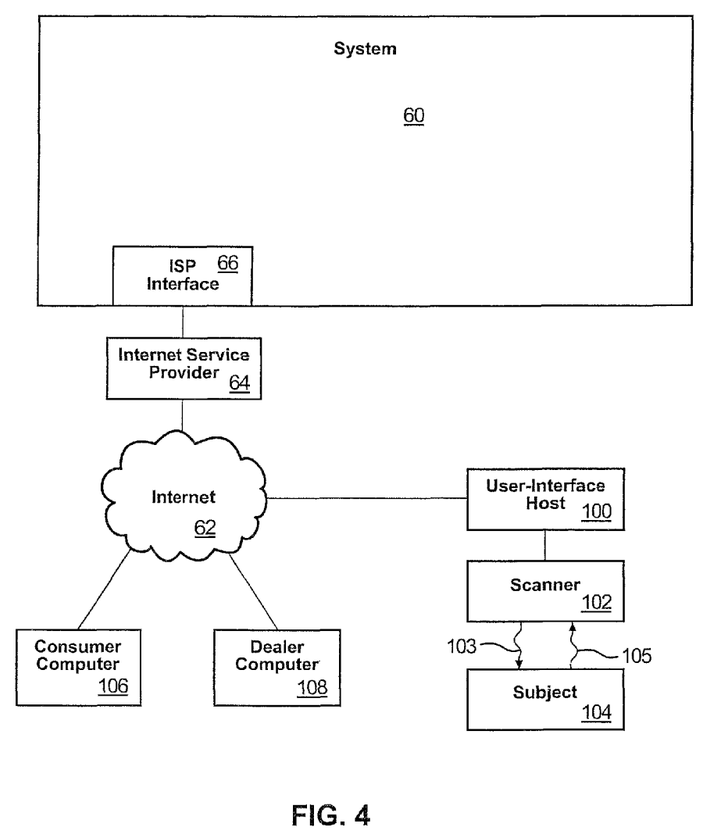
FIG. 4 is an alternative embodiment of a seamless, global, tracking system in accordance with the present invention, operable completely over Internet connections.

Referring to FIG. 4, in an alternative embodiment, the system 60 may connect strictly through the Internet 62. That is, consumer computers 106, and dealer computers 108 may access the Internet 62 in order to obtain access to the respective portals 88, 86 of the system 60. In yet another alternative embodiment, the consumer computer 106 and the dealer computer 108 may either one or both be connected through the telecommunication interface 68 to the system 60.

Figure 5:
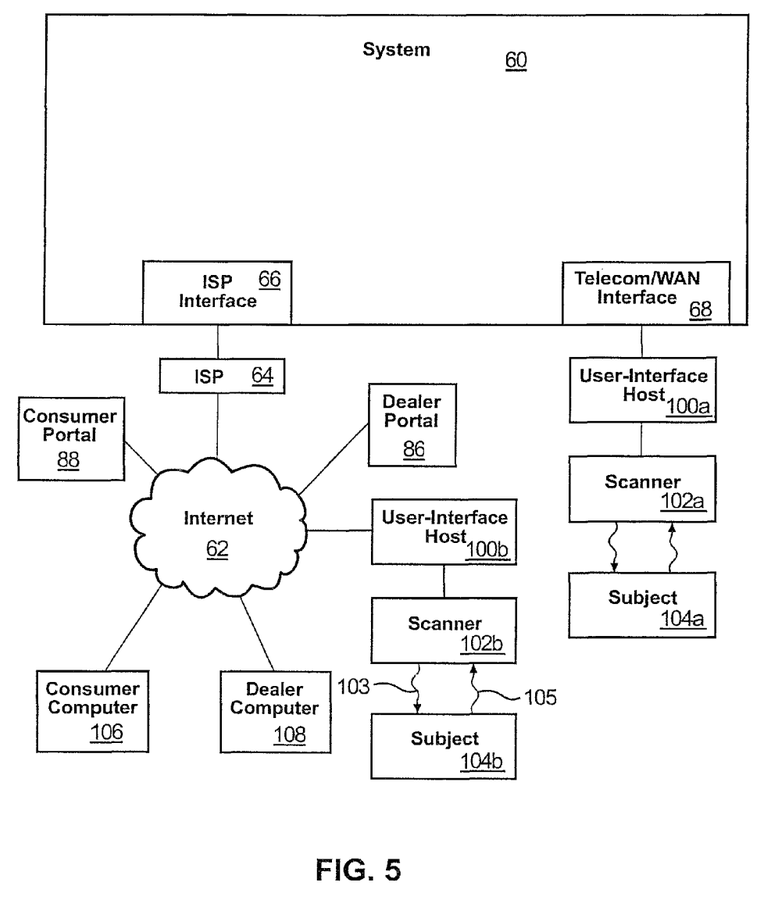
FIG. 5 is a schematic block diagram of an alternative embodiment of a reporting system in conjunction with a scanner system operable over the Internet and through direct connections.

Referring to FIG. 5, in yet another alternative embodiment, the system 60 may connect through a telecommunication interface 68 to one or more user-interface hosts 100a, supporting a scanner 102a for scanning a subject 104a. By the same token, the user-interface host 100b may connect through the Internet 62 and an ISP 64 in order to access the system 60. Many consider the Internet 62, absent appropriate measures, to be less secure than a direct line 69. Thus, in order obtain equivalent security, connecting through the Internet 62 may require additional software, signatures, and the like.

Figure 6:
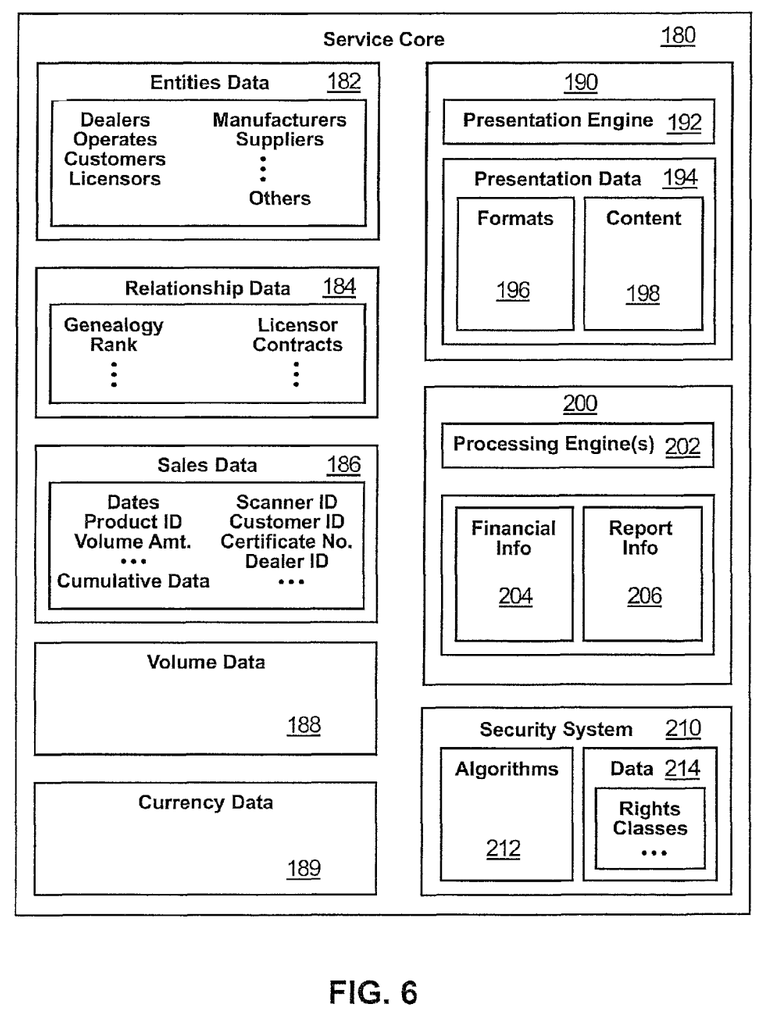
FIG. 6 is a schematic block diagram of a service core including data for managing sales and scanning information.

Referring to FIG. 6, a method and apparatus in accordance with the invention may include a service core 180. In order to operate the system 60, entities data 182 may be maintained by the database 70. Entities data 182 may include information regarding dealers, operators, customers, licensors, manufacturers, suppliers, and others. Relationship data 184 may include genealogy (multi-level marketing relationship lines, etc., for example), rank (e.g., based on organizational size, depth, production volume, etc.) of an individual or entity on which compensation (for example) may be based. Licensure, including licensors and licensees, contracts, and other information may be included in relationship data 184. The relationship data 184 is particularly important for communication and for compensation.

Sales data 186 may include dates of events, such as presentations, sales, scans, and the like. Likewise, the data 186 may include product identification, volume amounts of particular products, a normalized volume amount that relates more to dollar volume, and cumulative data over various periods of interest in sales or other activity. Similarly, sales data 186 may include scanner identification, customer identification, certificate numbers, dealer identification, and other information that may assist in relating sales to entities 182 and relationships 184.

Likewise, volume data 188 may be thought of as any and all information that may be useful in determining sales performance of individuals and entities. Since relationship data 184 includes genealogy relationships between dealers in the organization, the volume data 188 associated with each of those individuals may depend on those relationships. For example, the commission for a sale directly to a consumer dealer may be a higher, typically, than a commission paid to that same dealer on the same sale.

Nevertheless, as volumes increase within a particular dealer or manager's organization, the rates of compensation for volumes may increase, as an incentive. Thus, the volume data 188 may be intermediate information from sales data 186 to identify key information that may be required for compensation schemes and schedules. Volume data 188 may be the inputs, outputs, or both for compensation equations. The volume data 188 may be raw data, or may be intermediate data incorporating both sales data 186 and relationship data 184, or may be a combination thereof.

Inasmuch as marketing is becoming a global enterprise, currency data 189 may be important. For example, in the service call 180, currency data 189 will be needed in order to provide compensation between individuals or other entities who have relationships defined by the relationship data 184 that span different countries. For example, Asia has several currencies. Similarly, Europe has had various currencies, although it is now trying to standardize on the Euro.

Nevertheless, it is not uncommon for individuals to have contacts across national boundaries and language boundaries, due to the availability of travel, and the communication of language. Thus, Latin American countries may have relationships spanning one or more countries. Similarly, dealers or others within the United States may have relationships with Europeans, Asians, Africans, Latin Americans, and so forth. Thus, the currency data 189 and the service call 180 provides for manipulation of compensation schemes in order to account for credits of payments in proper currencies.

The data 182, 184, 186, 188, 189 may be maintained in the database 70. Presentation systems 190 provide presentation graphics, data, formatting thereof, and the like. A presentation engine 192 may be programmed to provide presentation data 194 to any visitor to a consumer portal 88 or a dealer portal 86.

A presentation engine 192 interacts with an operator. The presentation data 194 may be thought of as including formatting 196, and content 198.

Likewise, processing systems 200 are important for handling information transfer. For example, a database engine 72 often contains very sophisticated programming in a number of different library or other executable programs in order to intake, output, and manage database records 74. Some of the requirements presently contemplated for a processing system 200 may include a processing engine 202 programmed to process information such as financial information 204 and report information 206.

Financial information 204 may include raw data, partially processed data, personal data, and the like for any individual consumer, dealer, organizational person, entity, or the like. Similarly, report information 206 may include information regarding sales volumes, marketing affiliations and individuals, and the like.

Typically, Internet systems available widely benefit from a security system 210. Executables 212 or algorithms 212 implementing security may operate in accordance with data 214 such as passwords, rights, classifications or classes of entities and individuals, classes of information, and the like. Thus, a security system 210 may execute algorithms 212 in order to verify, obtain, or operate in accordance with data 214 on which a security system 210 depends.

Figure 7:
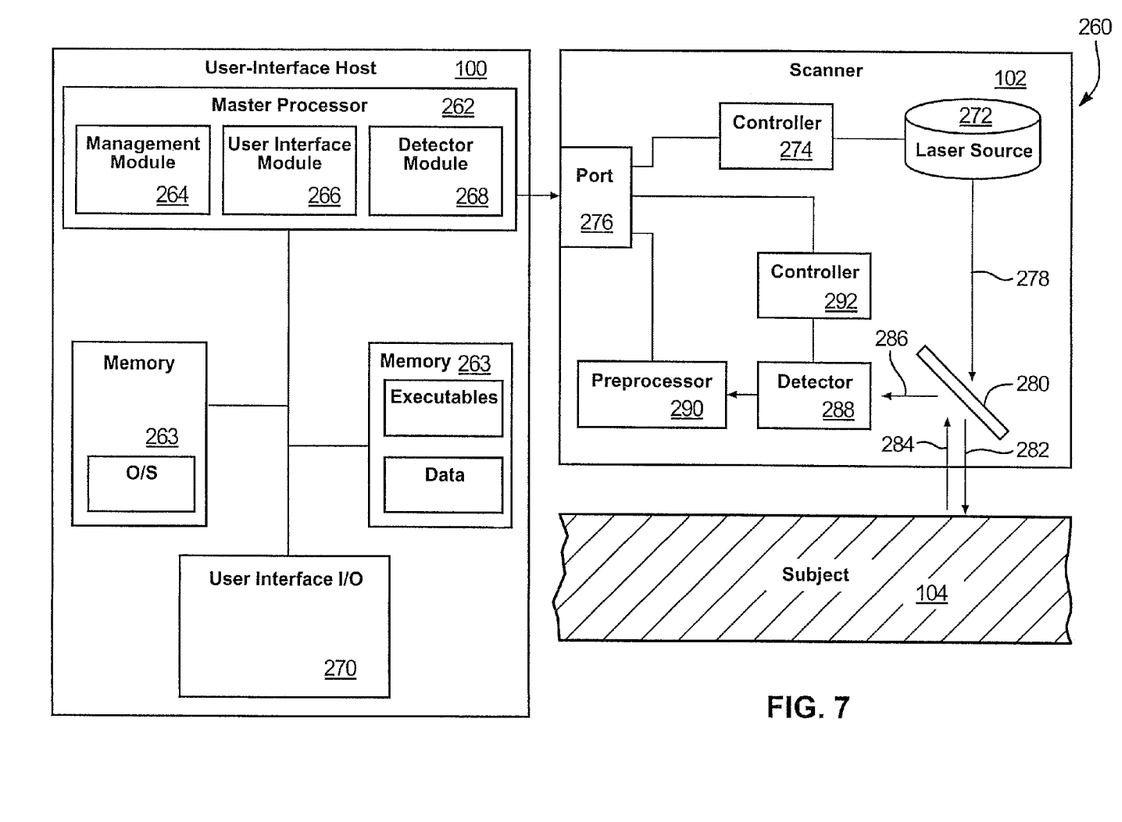
FIG. 7 is a schematic block diagram of one embodiment of a scanner and master processor that may operate as a scanning system and user-interface host in accordance with the invention.

Referring to FIG. 7, a user-interface host 100 or simply a host 100 may operate in conjunction with a scanner 102 as a system 260 for taking a survey or inventory of the hand, arm or other part of the skin of a subject 104. The subject 104 is typically a prospective consumer. The details of operation of the scanner 102 are disclosed by Gellerman (U.S. Pat. No. 6,205,354). A simplified schematic will suffice here. In general, a master processor 262 may be thought of as the CPU or processor within a host computer 100. Typically, the master processor 262 needs to accomplish several functions.

For example, a management module 264 may execute on a processor 262 in order to manage the entire process. A presentation 190 may be programmed to run on the processor 262 of the host 100. A processing system 200 may be programmed into the processor 262 to handle various information.

Primarily technical information is processed from the scanner 102, and information available to a user is presented. Accordingly, a management module 264 may manage the order of presentation information, may include the control in order to process both the information received from the scanner 102, and the input and output information to a user (operator). In one embodiment, the management module 264 is responsible for any of the functionality and allocation of resources of the processor 262.

Meanwhile, a user interface module 266 provides the presentation graphics, the information, the prompts, and the intake and outflow of information required to step through the sequence of events in which the host 100 and scanner 102 operate together. Similarly, a detector module 268 may be allocated any or all of the processing of information coming from the scanner 102, as well as processing the information to be provided to the user interface module 266 as output.

Numerous details are discussed later with respect to 10. Nevertheless, as a general proposition, the detector module 268 is responsible for data processing of information coming from the scanner 102. The user-interface module 266 is responsible for information presented to and retrieved from an operator. The management module 264 may control the operation of the processor 262, including control of the sequence of events conducted by the scanner 102, and may provide management of the interface between the user, the host 100, and the scanner 102.

A user-interface 270 may include any input and output systems. For example, keyboards, a mouse, data input and output devices, drives, screens, printers, and the like, may all be used in suitable arrangement as input, output, or both devices for interacting with an operator.

In general, a scanner 102 includes a laser source 272, which may be provided by any suitable means. For example, lasers may be large or small. Light emitting diodes can produce laser light. A laser source 272 may have some degree of control embedded in it or a controller 274 or controller 100. Typically, a laser source 272 may have some degree of local low level physical control. Other hardware in the scanner 102 or the host 100 may provide additional instructions at a higher level.

Eventually, the laser source 272 is controlled by signals received through a port 276 connecting the host 100 to the scanner 102. The module 264 may handle inputs, outputs, or both of the controller 274. Meanwhile, the laser source 272 projects a beam 278 to a director 280. The director 280 may or may not be necessary in various embodiments. In several embodiments, a splitter mirror may operate as a director 280 in order to pass the beam 278 through to become a beam 282 impinging on a subject 104.

As a result of the beam 282 striking the subject 104, a re-radiated or scattering beam (e.g. according to Raman scattering principles) returns as a beam 284 redirected by the director 280. The director 280 directs the beam 284 to become a beam 286 impinging on a director 288. Many intervening pathways, splitters, directors, filters, polarizing elements, and the like, may be implemented to meet the optical requirements of the beams 278, 282, 284, 286, any derivatives thereof, or contributions thereto. The Gellerman patent provides additional details of various embodiments for implementing a scanner 102.

Ultimately, a beam 286 impinges on a detector 288 providing a representation or signal output corresponding to intensities and frequencies of energy contained in the beam 286. As with the controller 274 on the laser source 272, the detector 288 typically will have some low level hardware controller 292 connected thereto in order to facilitate communication with other hardware within the scanner 102, the host 100, or both.

The detector 288 provides a signal 289 that may pass through a pre-processor 290. That is, depending on the sophistication desired to be programmed into hardware, firmware, or software within the scanner 102 proper, a pre-processor 290 may execute analysis of the information that is output as raw electrical signals 289 from the detector 288. Typically, a pre-processor 290 may include functions such as sampling, smoothing, filtering, and the like. Information from a pre-processor 290 is ultimately passed to the host 100, and specifically to the detector module 268. The detector module 268 is responsible for processing data originating with the detector 288. Again, the schematic of the system 260 of FIG. 7 is for logical and gross representation of the functionality. Many separate components in multitudinous arrangements can be used to implement the functional requirements of the system 260 in order to provide a reading. That reading or output may be characterized as a body defense score (BDS) corresponding to the carotenoid content in the subject 104.

In general, the device of Gellerman is directed toward detection of carotenoids in the skin. Nevertheless, other systems 260 may scan different parts of subjects 104, including other tissues, and the like. Thus, although one embodiment of an apparatus and method in accordance with the invention would include a licensure of the Gellerman technology for implementation in the system 260 as the scanner 102, other technologies may also be applied in other embodiments.

Figure 8:
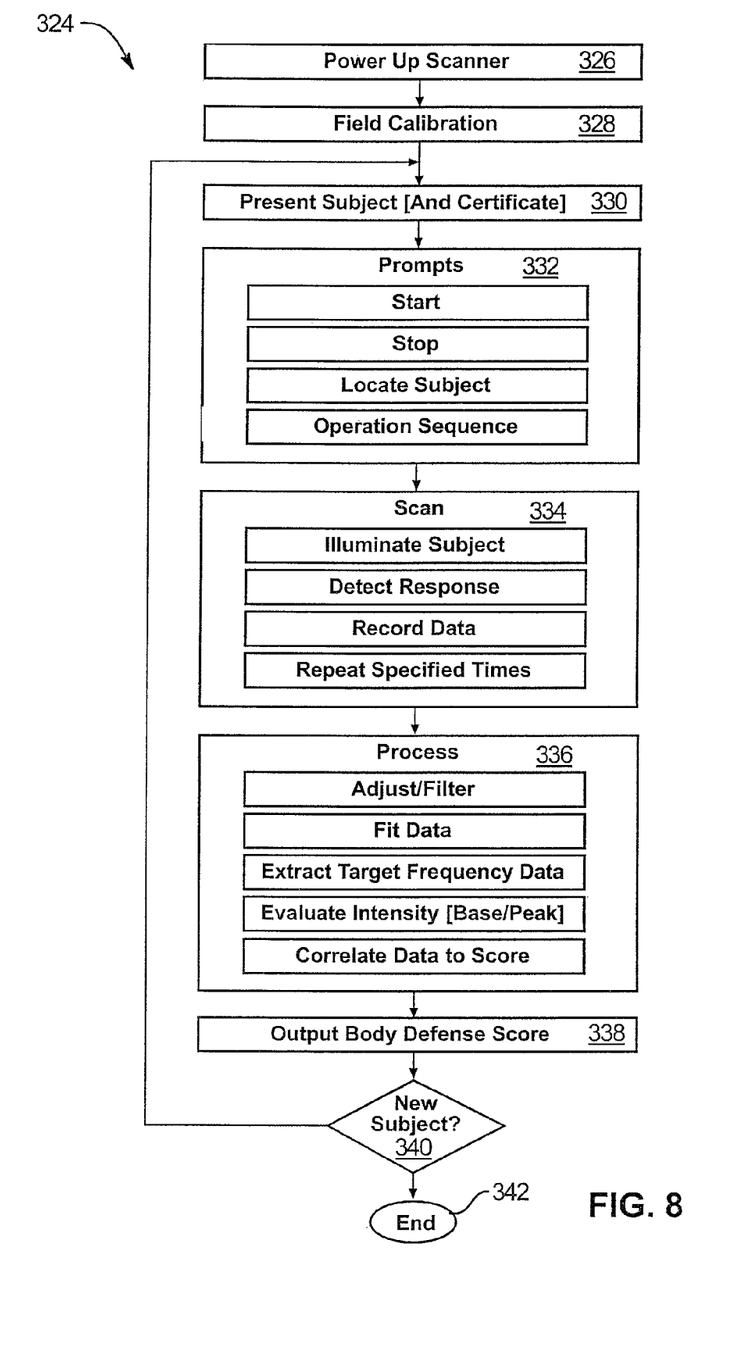
FIG. 8 is a schematic block diagram of one embodiment of a method of operation of a scanner and associated user-interface host connected thereto.

Referring to FIG. 8, operation methods 324 for the scanner 260 may include powering up 326 or turning on 326 the scanner 102. Although certain calibrations occur during manufacture, field calibration 328 may be valuable with each test, or each power up event 326, or periodically over time. Presentation 330 of a subject may or may not involve presentation of a certificate, shown in brackets as an optional step.

The prompts 332 may include various commands or images to direct the user, subject, or both. For example, indications of starting, locating a subject, or moving a subject's hand or arm closer, further, laterally about, in order to obtain a proper and reliable scan may be provided through prompts 332. Similarly, an operator may be provided indications of steps, waiting periods, operations to be conducted, keys to be struck, and other actions to be taken during, before, after, or in relation to the operation of the scanner. For example, prompted operational sequences may include operation of the scanner 102 as well as interaction with the SCG system 60, or even the sequence of dialing up the home system 60 in order to upload data.

Similarly, browsers, wizards, menus, steps through processes, and the like, may all be implemented with prompts 332 in order to reduce the level of complexity, and the degree of training required. In certain embodiments, the problems 332 may be largely graphical in order to transcend languages, and provide universal information.

A fundamental purpose of the scanner 102 is to scan 334 a subject 104. The scanner 102, may illuminate the subject, detect a response (illumination re-radiating or scattering back according to the Raman scattering theory from the subject 104), to provide a detectable result. The host 100 will process 336 the information in conjunction with the scanner 102. Data may be adjusted or filtered or the like. Similarly, data may be fit to a curve in order to provide a statistically reliable integration of multiple laser scans accomplished within a single scan 334 of a subject 104.

Extraction of data in the target frequency most commonly associated with the Raman scattering or other scattering technique that might be used by a scanner 102, may result in an ability to evaluate the intensity. Of most interest are the base and peak values of a particular portion of the charted intensity.

One objective is the correlation of the data to a score that is repeatable and meaningful to a subject 104. Accordingly, the correlation process and output on the BDS score or other meaningful output to a user may be part of the processing 336 of the significant data. Thus, an output 338 of a body defense score or other output metric may be done by a printed writing, a displayed image on a screen, a picture, a graph, or the like. If a new subject 104 is to be scanned, then a test 340 may return the process 324 to present 330 subject for scanning. Otherwise, the system may be shut down and end 342 its operation.

Figure 9:
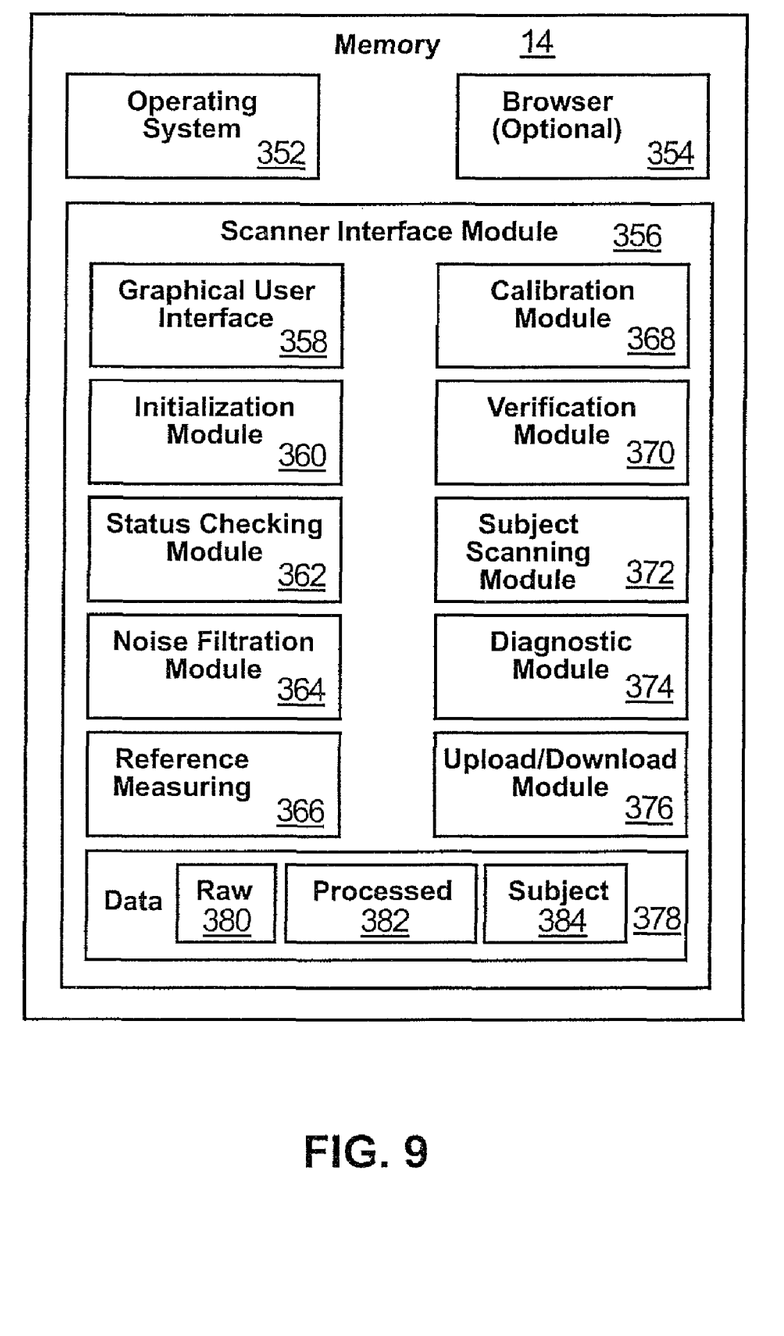
FIG. 9 is a schematic block diagram of one embodiment of a system of modules resident in memory of a computer in order to operate and integrate a system of scanning in accordance with the invention.

Referring to FIG. 9, a user-interface host 100, used to interface a scanner 102 to the global system 60, may be implemented using a laptop, notebook, personal digital assistant, such as a Palm Pilot or Ipaq, a digital tablet, or other dedicated computing device. In certain embodiments, the user-interface host 100 is an independent computing device that is physically separate from the scanner 102. However, in other contemplated embodiments, the user-interface host 100 may be integrated with the scanner 102 into a single device.

The user-interface host 100 may include various memory modules 14, including volatile memory such a RAM, or more permanent memory such as ROM, or magnetic storage such as floppy disks or hard drives. Memory 14 may contain executable and operational data 352, 354, 356 effective to control and operate the scanner 102, provide a graphical interface 358 for an operator, and communicate back to the seamless global compensation system 60.

For example, in certain embodiments, memory 14 may include an operating system 352 to perform basic system tasks, operate a file system, and provide an interface between applications and hardware components. The operating system 352 may be a common operating system 352, such as Windows or Linux, or may be a dedicated operating system 352 designed specifically to operate the scanner 102.

In certain embodiments, memory 14 may optionally include a browser 354. The browser 354 may be used in web-based systems to communicate with a central server 60, or servers 60. The browser 354 may also be used to directly communicate with a dealer portal 86, a consumer portal 88, or other Internet sites.

In accordance with the invention, a scanner interface module 356 may be provided in memory 14 to interface with the scanner 102. For example, a scanner interface module 356 may include a graphical user interface 358 for use by an operator. The graphical user interface 358 may display data to the operator, and may include forms or templates to receive inputs such as subject demographic information, operating variables, and the like.

An initialization module 360 may be used to initialize the scanner 102 before operation. For example, an initialization module 360 may read in parameter files and initialize key coefficients and variables used to operate the scanner 102. Some of these files may be created during a factory calibration process and copied to the user-interface host 100 upon "mating" a scanner 102 thereto. Selected files may be used while operating the scanner 102. Since every scanner 102 may have distinct characteristics and calibration specifications, a serial number may assigned to each scanner 102. When a scanner is operated, the serial number thereof may be compared to serial numbers stored in a configuration file to ensure that files correspond to the scanner 102 connected. Moreover, the initialization module 360 may verify that a scanner 102 is compatible with a version of software used in conjunction therewith.

The initialization module 360 may also initialize one or several communication ports between the user-interface host 100 and the scanner 102. In addition, coefficients and parameters may be read from the scanner's memory for analysis on the user-interface host 100.

A status checking module 362 may retrieve various status from the scanner 102. For example, a status checking module 362 may retrieve the serial number, or other identifying value, of an attached scanner 102 to verify that the scanner 102 is the device originally, initialized. Additionally, the status checking module 362 may check various status of the laser 272, such as temperature, or may verify that the scanner 102 is sufficiently "warmed up." Certain returned values may indicate that a scanner 102 is connected and communicating with the user-interface host 100. Other values may indicate that operation parameters are within prescribed limits, thus ensuring that subsequent scans will return accurate and consistent data. The status checking module 362 may be primarily dedicated to checking values of key indicators at any selected point in time.

A noise filtering module 364 may be used to filter noise from data gathered by a scan. For example, in certain embodiments, a "dark scan" may be used to filter noise from subject 104 scans. Raw data values collected during a dark scan may be subtracted from raw data values collected during a subject 104 scan, pixel by pixel, thereby producing a "dark corrected" scan.

The noise filtering module 364 may perform a "dark scan" in response to various conditions such as to see if it is sufficiently warm and stable, whenever a scanner 102 is recalibrated, or when it seems to be drifting.

A reference measuring module 366 may perform scans used in a calibration process. For example, a reference scan may establish variable and coefficient values, such that results (e.g. scores provided to scanned customers) are substantially equivalent to values that would have been produced at the factory.

A calibration module 368 may be provided to calculate, modify, and test important parameters used in the computation of a subject score. A subject score refers to an assessment or measurement of the health of some aspect of a subject 104 (customer). For example, in accordance with the present invention, a scanner 102 may provide a score indicating the amount of carotenoids present in the skin of a subject 104. However, the score need not refer to carotenoids, but may refer to any measurement or assessment of the health of a patient.

The scanner 102 may compute a score, such as a body defense score of a subject 104. In addition to raw data measured from the subject 104, the score may be calculated using inputs generated by the factory calibration process, the reference measurements 366, and the noise filtering 364.

A verification module 370 may be used to verify that a scanner 102 is properly calibrated. For example, a reference material, such as a card or other material having a known concentration or level of carotenoids, may be used to calibrate the scanner 102. The scanner 102 may be calibrated with the reference material at the factory. In one embodiment, a synthetic material giving the same response as carotenoids has been shown to serve as a calibration material. It may be compounded to behave as if no carotenoids are present, a low value, or a high value. When recalibrated, the scanner 102 may again measure the concentration in the reference material.

A subject scanning module 372 may be responsible for performing scans on subjects 104. For example, the subject scanning module 372 may enable a normal scan on the skin of a subject's hand in order to return a body defense score. The subject scanning module 372 may also verify that the serial number from an attached scanner 102 is the same as the scanner 102 originally initialized to further ensure accuracy of the score. Various operating parameters such as temperature, laser status, and the like, may be checked to verify that the scanner 102 is ready to produce reliable data.

In certain embodiments, the subject scanning module 372 may perform a pre-scan for a prescribed period, such as 20 seconds, to "bleach" the subject's skin. Next, a data acquisition scan may be performed various times, with a body defense score calculated after each. These scores may be averaged.

An operation may be performed to check for scan transmission errors. The scan may also be "dark corrected" using data calculated by the noise filtering module 364. If excessive luminescence is detected that is out of range of the scanner 102, a scan may be stopped. If a scan is successful, data obtained therefrom may be analyzed to calculate a body defense score. A test may be performed on data received from a scan to determine if there is a significant difference in any of the several body defense scores taken of a subject 104. If a significant difference is detected, an error message may notify an operator.

A diagnostic module 376 may diagnose problems, settings, or status of the scanner 102, such as a communications rate, or baud rate, of the scanner 102. Various commands may be sent to the scanner 102 to monitor the response thereof, in order to ascertain that the scanner 102 is operating correctly.

Other commands may be sent to retrieve the serial number of the scanner 102, or to retrieve the version numbers of scanner firmware and hardware components. Yet other commands may retrieve the temperature, set integration times, set coefficients, turn a laser 272 on or off, return a recently computed body defense score, return raw data, or return peak data computed from raw data.

An upload/download module 376 may function to upload subject data, such as body defense scores or demographic data, to a remote server, such as to the uploaded data files server 76. The module 376 may further coordinate the download, from remote servers such as the software update server 78, of newer versions of software to operate the scanner 102.

The scanner interface module 356 may be further programmed to store data 378. Data 378 may include raw data 380 gathered by the scanner 102, processed data 382 such as body defense scores and the like, and subject data 384, such as demographic data corresponding to each subject 104.

The present invention may be embodied in other specific forms without departing from its essence or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

Wherefore, we claim:

1. An apparatus for online data collection and management of testing and test data from re-radiation responses of biological tissue in-vivo, the apparatus comprising:
   at least one testing device to take measurements, non-destructively, non-invasively, and in-vivo, by detection of a re-radiation response of a selected molecular structure present in biological tissue of a subject;
   a computing device operably connected to the at least one testing device, the computing device comprising a processor and a non-transitory computer-readable storage medium having computer executable programming instructions stored therein to be executed by the processor, the computer executable programming instructions comprising:
   programming instructions to provide prompts to an operator of the testing device directing a sequence of actions to be carried out by the operator with respect to operation of the at least one testing device and positioning of the subject to obtain reliable measurements, and
   programming instructions to provide analysis of the measurements and score correlation to determine as output data a body defense score, which corresponds to a relative level of nutrient intake of the subject and delivery to the biological tissue thereof, the nutrient corresponding to the selected molecular structure;
   a communications device to transmit, over the Internet, output data reflecting the analysis from the computing device to a remote location for storage and processing;
   and a server operably connected over the Internet to the computing device through the communications device to receive for storage and processing output data reflecting the measurements corresponding to a plurality of subjects;
   and the server further programmed to provide the output data directed to the subject in consequence of the measurements.

2. The apparatus of claim 1, wherein the server is further programmed to track, analyze, and distribute compensation corresponding to administration of nutritional supplements related to the molecular structure.

3. The apparatus of claim 2, further comprising:
   a plurality of testing devices assigned to operators thereof, wherein:
   testing devices of the plurality of testing devices are mobile and independent from one another, and
   each testing device is configured to perform tests by non-destructively illuminating and measuring a radiant response from live tissue in vivo and to determine a corresponding value reflecting concentration of the selected molecular structure relating to nutrition of subjects.

4. The apparatus of claim 3, wherein the computing device is further programmed to be controlled against unauthorized use by codes received from the server and corresponding to the uploading of the data to the server.

5. The apparatus of claim 4, wherein the server is further programmed to host a database to collect and manage the data corresponding to a plurality of subjects, a plurality of the computing devices and associated testing devices, operating at arbitrary times and places, the database being programmed to track the subjects, the data corresponding to each subject.

6. A method for tracking and controlling over the Internet testing of individuals for levels of nutrients, the method comprising:

providing, to an operator, a Raman scattering testing device effective to measure non-destructively, in-vivo, and non-invasively a chemical constituent of tissue in a subject;

providing a user interface host, the user interface host comprising a processor and a non-transitory computer-readable storage medium having computer executable programming instructions stored therein to be executed by the processor, the computer executable programming instructions comprising: programming instructions to provide prompts to the operator directing a sequence of actions to be carried out by the operator with respect to operation of the testing device and positioning of the subject to obtain reliable measurements;

providing said prompts to the operator via the user interface host;

measuring, by the operator, the radiant response of the chemical constituent, non-destructively, non-invasively, and in-vivo, by detection thereof in tissue of the subject;

analyzing on a computing device the measurements to determine a comparative nutritional level of the subject corresponding to the chemical constituent of the subject;

transmitting, over the Internet, data reflecting the analysis to a server located at a remote location for storage and processing; and     processing the data reflecting the analysis to provide as output a body defense score of the subject in consequence of the measurements, said body defense score being a relative value based in part on score correlation using previous measurement data stored at the server.

7. The method of claim 6, further comprising providing, to the subject, a health supplement directed to altering the level of the chemical constituent in consequence of the measurement.

8. The method of claim 7, further comprising tracking, analyzing, and distributing over the Internet compensation corresponding to administration of the nutritional supplements.

9. The method of claim 8, further comprising:

controlling over the Internet a plurality of testing devices assigned to operators thereof against unauthorized use by codes received from the server and corresponding to the uploading of the data to the server.

10. The method of claim 9, further comprising;

managing over the Internet a database to collect and manage the data corresponding to a plurality of subjects, a plurality of the computing devices and associated testing devices, operating at arbitrary times and places, the database being programmed to track the subjects, the data corresponding to each subject.

* * * * *